United States Patent [19]

Hearst

[11] Patent Number: 4,738,538

[45] Date of Patent: Apr. 19, 1988

[54] GLOSS MEASUREMENT DEVICE

[75] Inventor: Peter J. Hearst, Oxnard, Calif.

[73] Assignee: The United States of America as represented by the Secretary of the Navy, Washington, D.C.

[21] Appl. No.: 6,517

[22] Filed: Jan. 23, 1987

[51] Int. Cl.⁴ ............................................. G01N 21/47
[52] U.S. Cl. ..................................................... 356/446
[58] Field of Search ....................... 356/445, 446, 124.5

[56] References Cited

U.S. PATENT DOCUMENTS

| | | | |
|---|---|---|---|
| 1,949,619 | 3/1934 | Pfund | 356/446 |
| 2,830,490 | 4/1958 | Pellegrini | 356/446 |
| 3,396,627 | 8/1968 | Rouy et al. | 356/446 |
| 3,549,264 | 12/1970 | Christie | 356/446 |

Primary Examiner—R. A. Rosenberger
Assistant Examiner—Steve McGowan
Attorney, Agent, or Firm—Louis Allahut; Joseph M. St.Amand

[57] ABSTRACT

A simple inexpensive gloss measurement device which makes use of the measurement of a maximum angle of view of a clear reflection to obtain a measurement of gloss, consists of an instrument of L-shaped configuration with one or more small images (e.g., hollow squares) on the lower portion of the shorter arm and a graduated scale along edges of the longer arm. The device is placed on a coated surface to be measured, with the images close to the surface of the coating. The highest angle of view at which reflection of the images on the coating can be clearly recognized is noted on the graduated scale as a measure of the gloss of the coating.

20 Claims, 2 Drawing Sheets

GLOSS MEASUREMENT DEVICE

BACKGROUND OF THE INVENTION

The invention relates to gloss measuring devices and more particularly to a simple, inexpensive instrument for measuring the gloss of coatings.

Gloss is a measure of the light that is reflected from a surface. Gloss is usually determined according to ASTM D 523, Specular Gloss. For coatings, the 60-degree gloss is typically measured. The light reflected at 60 degrees from the vertical is compared to the light incident at 60 degrees from the vertical, and the ratio is expressed as a percentage of the reflection that would be obtained from polished black glass.

The amount of light reflected from a coated surface is very dependent on the angle of reflection. Viewed at very low angles (or at angles approaching 90 degrees as measured from the perpendicular), flat coatings or even roadway surfaces may give mirror-like reflections. Thus, for flat coatings, the 85-degree gloss is measured, and for high gloss coatings, the 20-degree gloss may be measured. Portable photometric instruments presently used for each of these measurements are expensive.

There are a number of devices available for measuring gloss, all of which are complicated and expensive apparatus having both electrical and mechanical components. Prior to the present invention, there was no good way of measuring in the field without expensive instrumentation, the gloss of a formulated coating.

SUMMARY OF THE PRESENT INVENTION

The present invention is an inexpensive instrument suitable for use by painters, etc., who are concerned about the quality of available coatings, and it requires very little skill or experience to operate. It provides a simple method to give information equivalent to that obtained with more expensive instrumentation.

The present invention makes use of the measurement of an angle of view to obtain a measure of the gloss. The gloss measurement device holds above the surface of a coating to be measured a row of small hollow squares (or other suitable images), which are reflected from the coating. The highest angle of view above the horizontal at which the reflection of these squares in the coating can be clearly recognized is noted on a scale of the device. This maximum angle of view is a measure of the gloss of the coating. The flat surface holding the squares and the flat surface holding the scale are joined perpendicularly into a simple L-shaped instrument.

It is an object of the invention, therefore, to provide an uncomplicated and low-cost measuring device, which is simple to operate, for determining the gloss or equivalent properties of applied coatings or of other surfaces.

Further features and advantages of the invention will becom apparent from the description below.

BRIEF DESCRIPTION OF THE DRAWINGS

The invention is illustrated by way of example only, in the accompanying drawings, wherein.

DESCRIPTION OF THE PREFERRED EMBODIMENT

Figure 1:
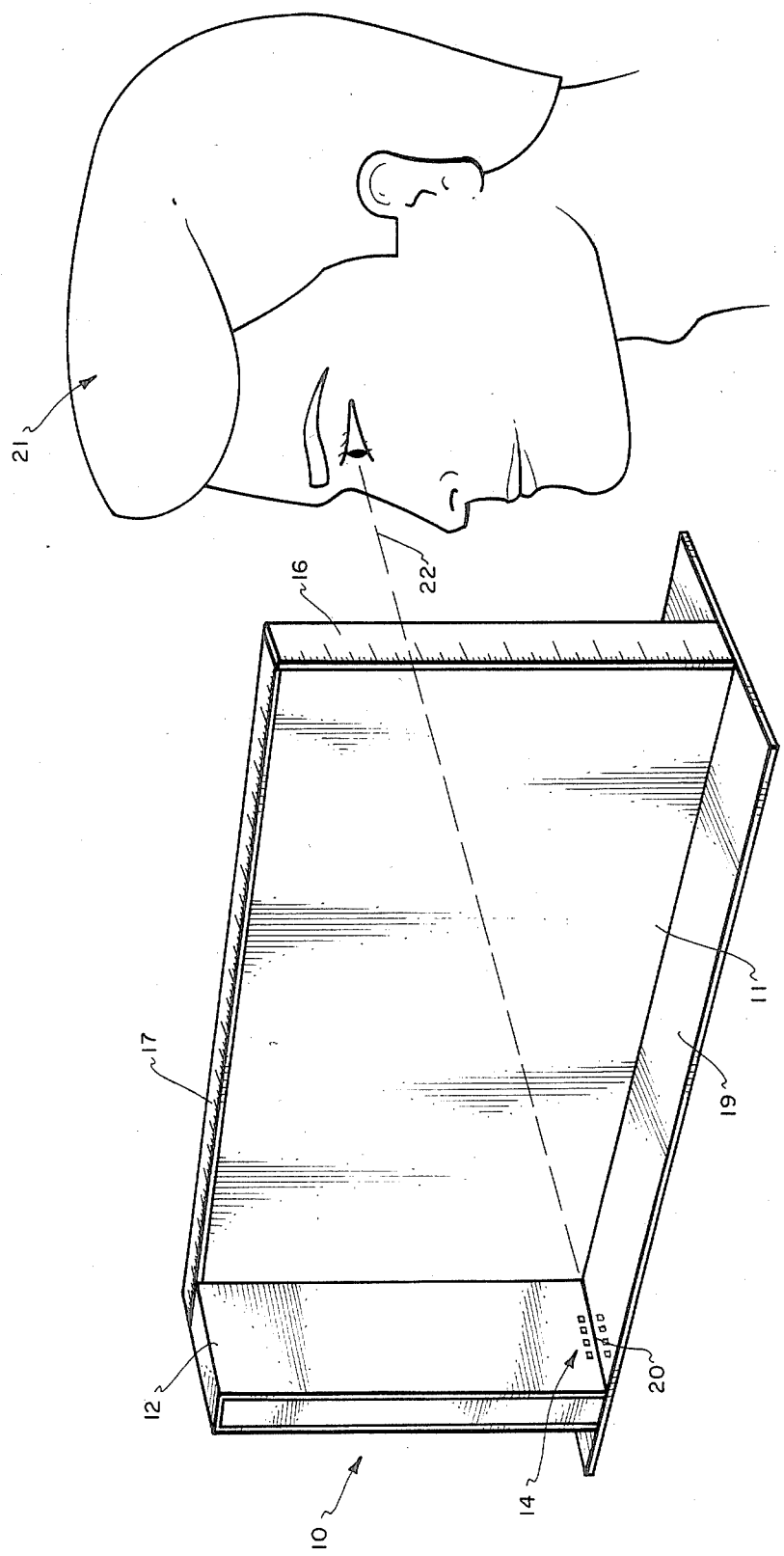
FIG. 1 is a perspective view of the gloss measurement device.

The gloss measuring device illustrated in FIG. 1 measures the maximum angle of view, measured from the horizontal, at which a specified reflection can be seen, rather than measuring the amount of light reflected from the coating at a specific angle. Whether a coating finish or texture is flat, eggshell, semigloss, gloss, or high gloss determines this maximum angle of view, and the value of the maximum angle of view increases in this order, as listed. A very glossy coating may show a mirror-like reflection perpendicular to the coated surface. As coatings become less glossy, the line-of-sight angle at which a reflection is seen drops down from the vertical position and becomes more parallel to the coating.

The device 10, shown in FIG. 1, consists essentially of two flat surfaces or panels 11 and 12 mounted at right angles to each other and forming an L-shaped instrument. Panels 11 and 12 can be made from any suitable material, such as, plastic, stiff cardboard, fiberboard, wood, metal, etc. The sizes of surfaces 11 and 12 are not critical. A 10-centimeter high and 20-centimeter long (4×8 inch) surface 11 and a 10-centimeter high and 5-centimeter wide (4×2 inch) surface 12 joined perpendicularly will be suitable. On the inside of the short leg 12, at 2 millimeters above the bottom (i.e., the surface to be measures), are located four hollow black squares 14 (with 1.5-millimeter sides) on a white background. Squares 14 can be substituted with any suitable images that may reflect clearly from a coating to be measured. The images 14 can be made on white paper, for example, which is then attached to surface 12 by any suitable means. The 1.5-mm hollow black squares, placed 1.5 millimeters apart, effectively have 0.9-millimeter white squares in their centers. The image or images 14 can be formed by any suitable means directly onto or into leg 12, or leg 12 can be otherwise shaped to provide a suitable image or images for effectively reflecting from the surface to be measured, as hereinafter described.

At the end of the long leg 11 is a graduated 10-centimeter scale 16, and this scale is continued along the top 17 of leg 12 with graduations from 10 to 30 centimeters. The scale along edges 16 and 17 also can be graduated in angles of view (where 5 degrees would be at 1.6 cm, 10 degrees at 3.5 cm, etc), or the ranges of various gloss ratings of coatings can be indicated, as desired. The scales 16 and 17 can be extended onto the face of surface 11, as desired, and also marked according to the various gloss ratings, such as flat, eggshell, semigloss, gloss, high gloss, etc.

Measurements are made by setting the instrument 10 on a flat coated surface 19, the gloss of which is to be measured. The user 21, as shown in FIG. 1, looking at the set of squares 14 (or other suitable images) on the inside surface of leg 11 from a high angle of view, lowers the angle of view until a reflection of squares 14 appears below the squares in the coating 19, and then lowers the angle of view slightly more until the reflection clearly shows that the squares are hollow. A reading is now taken, at the position on the scale 16 & 17 that appears to be intersected by the line 20 formed by instrument 10 resting on the coating 19 (i.e., the line between the squares on the instrument and the squares reflected in the coating), which is the position where the line of sight 22 between the eye of the viewer 21 and line 20 passes the scale 16 or 17. The scale reading is taken at the highest angle of view at which it is clear that the squares are hollow. For measuring the angle of view at which a reflection can be seen in a coating, by sighting with the simple instrument described above, the coating can be applied on an opacity chart.

The amount of light reflected from a coated surface is very dependent on the angle of reflection. Viewed at very low angles (or at angles approaching 90 degrees as measured from the perpendicular), flat coatings or even roadway surfaces may give mirror-like reflections. Therefore, the high gloss of automotive lacquers is generally measured at 20 degrees, whereas 60-degree gloss is usually measured for gloss or semigloss coatings, and 85-degree gloss is measured for flat coatings.

Gloss is usually determined according to ASTM D 523, Specular Gloss, using a gloss meter, which measures the relative amount of light reflected from a coating, compared to that reflected from polished black glass.

The visual gloss measurement instrument 10 of this invention, described above, essentially measures the highest angle of view at which a set of images (such as hollow squares 14, FIG. 1), placed in a selected manner, can be recognized by the eye of the viewer. Although the scale 16 & 17 of FIG. 1 is calibrated in centimeters, it could as well be calibrated in degrees or gloss range. The readings obtained are obviously somewhat dependent on the eyesight of the viewer, but nevertheless provide reasonably accurate measurements. If preferred, the scale formed along the edge of panel 12 can be made on one continuous smooth curve rather than as sections 16 and 17 which join at right angles.

Figure 2:
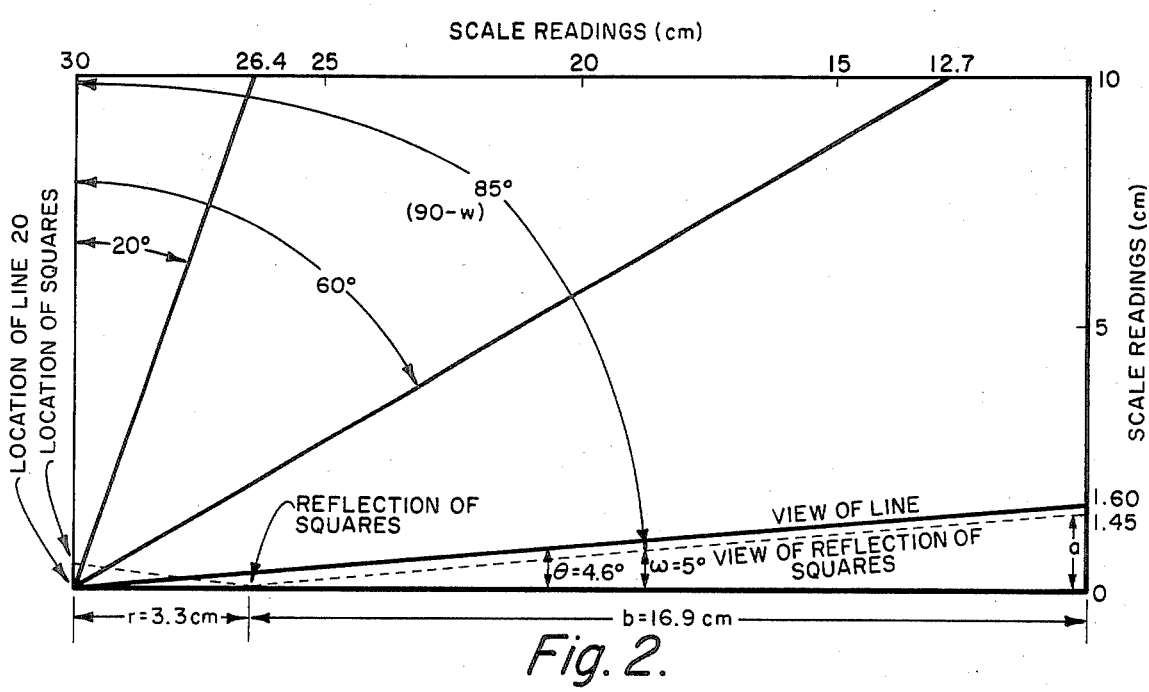
FIG. 2 is an illustration of the angles of view of reflections in visual gloss measurements using the instrument of FIG. 1.

The angles of view of the reflections in the visual gloss measurement device of FIG. 1 are shown in FIG. 2. Calculated angular equivalents of some scale readings are given in Table 1, below:

surface of coating 19, as well as the 1.45 cm scale height of the view of the reflections and the 1.6 cm scale height of the view of the line of contact of the instrument with the coating. The 4.6 degree angle of view of the line differs appreciably from the 5 degree angle of reflection, but this difference becomes insignificant at higher angles of view. At a 30-degree angle of reflection, which is the angle for a 60-degree gloss reading, the scale reading is 12.7 cm. The equivalent scale reading for a 20-degree gloss reading is 26.4 cm, also illustrated in FIG. 2.

There is no direct relationship between the 60-degree gloss and the 85-degree gloss of a coating. Therefore the visual gloss measurements cannot correlate equally as well with both types of gloss values. It would be expected that observed scale readings near 1.6 cm would correlate better with 85-degree gloss values and that observed scale readings near 12.7 cm would correlate better with the 60-degree gloss values of the coatings.

Figure 3:
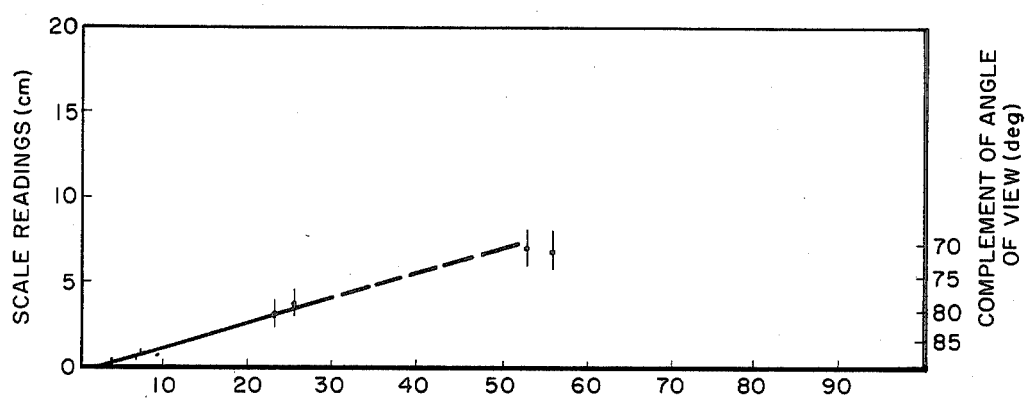
FIG. 3 is a curve showing the comparison of gloss measurement with 85-degree gloss values.
Figure 4:
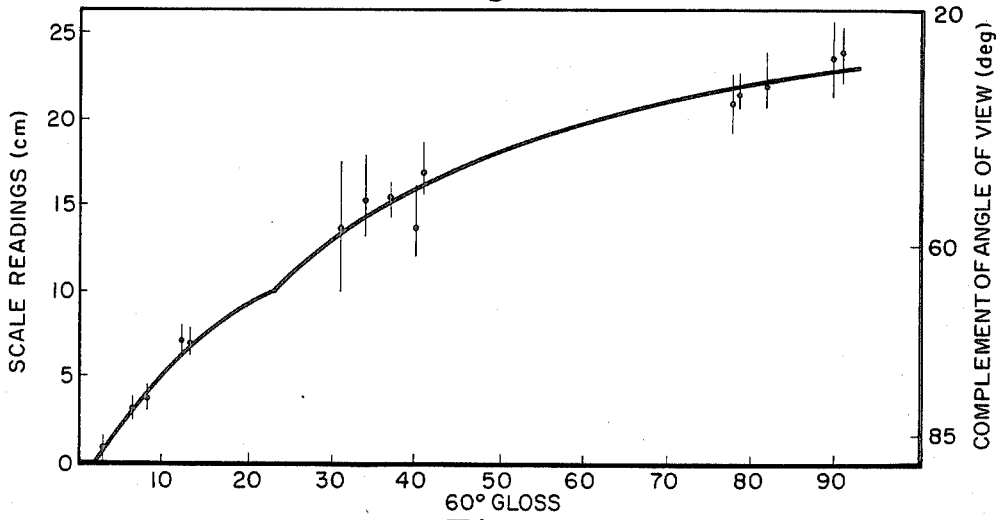
FIG. 4 is a curve showing comparison of gloss measurements with 60-degree gloss values.

The comparison of the visual results with the 85-degree gloss values of 9 coatings, in FIG. 3, and with the 60-degree gloss values of 19 coatings, in FIG. 4, show that the above expectations are borne out. The visual results correlate well with 85-degree gloss values of up to about 30 or higher. (Comparisons of higher scale readings with 85-degree gloss values were not made in FIG. 3 because the complements of the angles of view, as shown at the right ordinate scale, soon become much smaller than 85 degrees.)

The curve relating the scale readings to 60-degree gloss values (FIG. 4) was drawn with an inflection at a scale reading of 10, where the scale on instrument 10 changes from vertical to horizontal (i.e., from scale section 16 to scale section 17). As shown by the calculated values in Table 1, the effect of a one-degree change in angle below that scale reading is 0.44 cm, whereas the effect of a one-degree change above that scale reading is 0.84 cm. Therefore the slope of the curve should change by a factor of 1.9 at the scale reading of 10 cm. The bars in FIGS. 3 and 4 show not only the average scale readings listed in Table 2, below, but also the range represented by one standard deviation.

TABLE 1

| Angles of View in Gloss Measurements[a] | | | | | | | | |
|---|---|---|---|---|---|---|---|---|
| Scale Reading[b] of | | Reflection Location[b] from | | Tangent of Angle of View of | | Angle of View of | | Complement of Angle of View (90-ω)[d] |
| Line (s) | Reflection (a) | Line (r) | Scale (b) | Line (s/20)[c] | Reflection (a/b) | Line (θ) | Reflection (ω) | |
| 1 | 0.85 | 4.5 | 15.5 | 0.0500 | 0.0548 | | 3.13 | |
| 1.5 | 1.35 | 3.5 | 16.5 | | 0.0818 | | 4.86 | |
| 1.61 | 1.46 | 3.3 | 16.7 | 0.0805 | 0.0874 | 4.60 | 5.00 | 85 |
| 2 | 1.85 | 2.5 | 17.5 | | 0.1057 | | 6.03 | |
| 3.53 | | 1.4 | | 0.176 | | 10.0 | | 80 |
| 5.36 | | | | 0.268 | | 15.0 | | 75 |
| 7.28 | | | | 0.364 | | 20.0 | | 70 |
| 9.56 | | | | | | 25.56 | | 64.44 |
| 10.00 | | 0.5 | | 0.500 | | 26.56 | | 63.44 |
| 10.84 | | | | 0.522 | | 27.56 | | 62.44 |
| 12.7 | 12.5 | 0.3 | | 0.577 | | 30.0 | | 60 |
| 26.4 | | | | 2.747 | | 70.0 | | 20 |

[a]Scale readings of the reflections (a), at given scale readings of the line (s), and the distance of the reflections from the location of the squares (r) were experimental values, except for the third set which was calculated. All other values were calculated as explained in the discussion section of the text.
[b]Distances in cm.
[c]For scale readings of 10 or less. (For scale readings of 10.84, 12.68, and 26.36, the fractions are 10/19.16, 10/17.32, 10/3.64, respectively.)
[d]For values of ω of about 10 or higher, the value of (90-θ) is listed instead of the nearly equal value of (90-ω).

The view of a reflection at an angle of 5 degrees (at which 85-degree gloss measurements are made) is depicted in FIG. 2, which illustrates that the point of reflection of the squares 14 is at 3.3 centimeters away from the line of contact 20 of instrument 10 with the

TABLE 2

Gloss Measurements

| Gloss of Coated Chart[a] | | Individual Scale Readings[b] | | | | | Average Scale Readings[c] | |
|---|---|---|---|---|---|---|---|---|
| 60° | 85° | 1 | 2 | 3 | 4 | 5 | Value | Standard Deviation |
| 2.3 | 2.7 | 0.5 | 0.2 | 0.5 | 0.4 | 0.3 | 0.4 | 0.13 |
| 2.7 | 6.4 | 1.0 | 0.6 | 1.2 | 0.9 | 0.9 | 0.9 | 0.22 |
| 2.8 | 0.8 | 0.0 | 0.0 | 0.2 | 0.0 | 0.0 | 0.0 | |
| 3.2 | 6.0 | 0.5 | 0.7 | 0.6 | 0.7 | 0.6 | 0.6 | 0.8 |
| 5.5 | 9.4 | 0.8 | 0.8 | 0.8 | 0.7 | 0.8 | 0.8 | 0.4 |
| 6.4 | 23.2 | 3.1 | 3.7 | 3.8 | 3.0 | 2.6 | 3.2 | 0.50 |
| 8.0 | 25.4 | 3.5 | 4.0 | 3.5 | 3.4 | 4.8 | 3.8 | 0.58 |
| 12.3 | 52.8 | 6.5 | 6.5 | 6.9 | 6.3 | 8.9 | 7.0 | 1.07 |
| 13.0 | 55.7 | 7.1 | 5.5 | 7.0 | 6.3 | 8.1 | 6.8 | 0.97 |
| 31 | 72 | 11.0 | 8.5 | 18.5 | 14.0 | 15.6 | 13.5 | 3.9 |
| 34 | 65 | 13.0 | 12.0 | 17.4 | 16.0 | 18.0 | 15.3 | 2.7 |
| 37 | 62 | 13.4 | 16.0 | 15.6 | 16.0 | 15.5 | 15.3 | 1.1 |
| 40 | 66 | 13.5 | 14.0 | 15.7 | 16.5 | 9.4 | 13.8 | 2.8 |
| 41 | 71 | 15.5 | 16.5 | 18.8 | 18.0 | 15.5 | 16.9 | 1.5 |
| 78 | 73 | 21.0 | 20.0 | 23.7 | 22.0 | 18.0 | 20.9 | 2.1 |
| 78 | 91 | 21.5 | 21.0 | 23.4 | 22.0 | 20.0 | 21.6 | 1.2 |
| 82 | 90 | 20.0 | 21.0 | 24.6 | 24.0 | 22.0 | 22.3 | 2.0 |
| 90 | 100 | 24.8 | 21.0 | 25.5 | 25.3 | 20.2 | 23.4 | 2.5 |
| 91 | 102 | 22.5 | 23.5 | 26.0 | 25.3 | 21.7 | 23.8 | 1.8 |

[a]Gloss of coating measured with 60° and 85° glossmeters.
[b]Gloss readings obtained by five individuals for each coated opacity chart.
[c]Average scale reading for each chart.

Although the visual gloss measurerments do not correlate as well with 60-degree gloss values as they do with 85-degree gloss values, the method is particularly useful for determining the gloss of eggshell, semigloss, and gloss coatings. The 60-degree gloss values for these categories of coatings are about 10 to 20, 40 to 70, and 75 or higher, respectively.

The gloss measurements made by five individuals and obtained with the visual gloss measurement instrument of FIG. 1 for various coatings are listed in Table 2, together with the average readings of the five individuals and the standard deviations. The 60-degree and 85-degree gloss readings of the same coatings as measured with glossmeters are also shown.

The main advantages of the method and instrument disclosed herein are the simplicity and low cost. This gloss measurement device is not intended to accurately reproduce the precise gloss values made by expensive photometric instruments. The device measures the highest angle of view at which a selected set of images, placed in a selected manner, can be recognized by the eye of the viewer. This angle of view may be as significant as, or even more significant than, the gloss values at a predetermined angle in determining the psychological reaction to the specular reflectance of a coating.

Obviously many modifications and variations of the present invention are possible in the light of the above teachings. It is therefore to be understood that within the scope of the appended claims, the invention may be practiced otherwise than as specifically described.

What is claimed is:

1. A device for determining the gloss or equivalent properties of applied coatings or of other surfaces, comprising:
   (a) a first means for holding above a surface to be measured at least one image that may be reflected from said surface to be measured;
   (b) a second means in connection with said first means for measuring the maximum angle of view from said surface to be measured at which a reflection of said at least one image from said surface can be clearly recognized by a viewer and a reading of said maximum angle of view observed; wherein the measured maximum angle of view is an indication of the gloss of said surface.

2. A device as in claim 1 wherein said at least one image is included as a part of said first means.

3. A device as in claim 1 wherein said first means comprises a white or light colored surface having at least one clear and distinct dark image thereon which is positioned above and is operable to clearly reflect from said surface to be measured.

4. A device as in claim 3 wherein said white or light colored surface is flat.

5. A device as in claim 1 wherein said second means comprises a surface located substantially perpendicular to said first means and includes scale means for reading the maximum angle of view observed.

6. A device as in claim 5 wherein said second means surface is flat.

7. A device as in claim 5 wherein said scale means is provided along at least one outer edge of said second means.

8. A device as in claim 7 wherein said scale means is provided on the substantially perpendicular surface of said second means.

9. A device as in claim 1 wherein the angle of reflectance of said at least one image on said first means from said coating to be measured is a measure of the gloss of the coating measured.

10. A device as in claim 1 wherein said first means holds a piece of paper having said at least one image printed thereon.

11. A device as in claim 1 wherein said device is shaped and is operable to be placed against the surface to be measured, and the maximum angle of view at which a specified reflection of said at least one image can be observed is measured from said surface to be measured to a line of sight between said viewer and a point of contact of said device with said surface to be measured which is below said at least one image on said first means.

12. A device as in claim 1 wherein said at least one image consists of a select set of images positioned in a select manner.

13. A device as in claim 1 wherein said first and second means are connected to form an L shaped instrument operable to be placed on a surface to be measured.

14. A device for determining the gloss or equivalent properties of applied coatings or of other surfaces, comprising:
   (a) a first means for holding above a surface to be measured at least one image that may be reflected from said surface to be measured;
   (b) a second means including a scale means thereon which is connected perpendicularly to said first means to form an L shaped instrument for measuring the maximum angle of view from said surface to be measured at which a reflection of said at least one image from said surface can be clearly recognized by a viewer and a reading of said maximum angle of view can be observed on said scale means thereon; wherein the measured maximum angle of view observed on said scale is an indication of the gloss rating of said surface.

15. A device as in claim 14 wherein said scale is provided on one continuous scale which can be readily observed by said viewer while clearly recognizing the reflection of said at least one image from the surface being measured; said reading being made where the line of view forming the maximum angle of view with the surface being measured intersects said scale.

16. A device as in claim 14 wherein said at least one image forms an integral portion of said first means.

17. A device as in claim 14 wherein said first means comprises a white or light colored surface having at least one clear and distinct dark image thereon which is positioned above and is operable to clearly reflect from said surface to be measured.

18. A device as in claim 14 wherein said at least one image is held perpendicular to said surface to be measured.

19. A simple and inexpensive method for determining the gloss or equivalent properties of applied coatings or of other surfaces, comprising;
    (a) the first step of, holding above a surface to be measured at least one image operable to be reflected from said surface to be measured;
    (b) the second step of, measuring the maximum angle of view from said surface to be measured at which a reflection of said at least one image can be clearly recognized by a viewer;
    (c) thirdly, converting the angular measurement of said maximum angle of view as measured in said second step into an indication of the type of surface measured by comparison of said angular measurement with a predetermined scale of angular readings representing gloss values, such as, flat, eggshell, semigloss, gloss, high gloss, etc.

20. A method as in claim 19 wherein the gloss ratings of flat, eggshell, semigloss, gloss, high gloss, etc., being measured of a surface is determined by said maximum angle of view; a very glossy surface showing a mirror-like reflectance at a near perpendicular angle of view to the surface being measured and said maximum angle of view gradually decreasing as the surface being measured becomes less glossy until said maximum angle of view becomes more parallel to said surface being measured for a flat gloss rating surface.

* * * * *